Aug. 25, 1953 W. B. MULHOLLAND ET AL Plant Pat. 1,212
AZALEA PLANT
Filed June 27, 1952
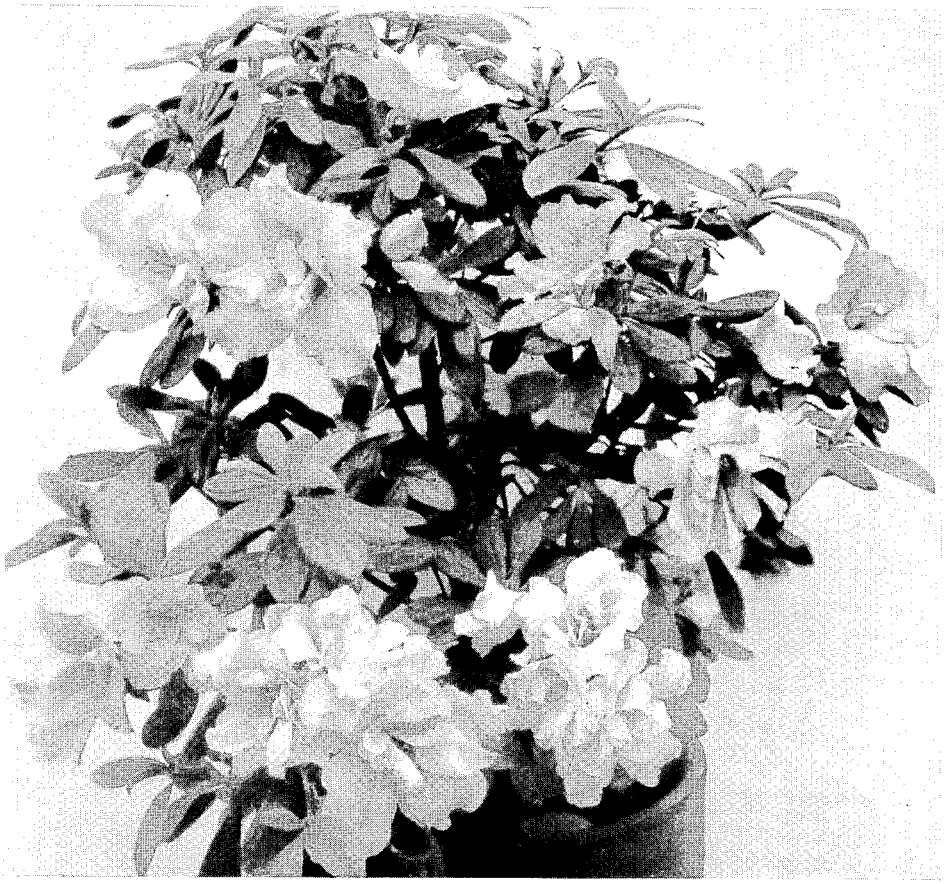
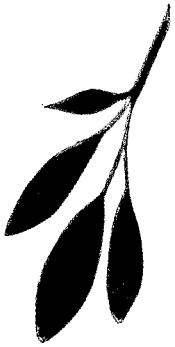
INVENTORS
William B. Mulholland
& Paul E. Shepp
By Orville M. Kile
Plant Pat. Agent.

Patented Aug. 25, 1953

Plant Pat. 1,212

UNITED STATES PATENT OFFICE 1,212

AZALEA PLANT

William B. Mulholland, Montebello, and Paul E. Shepp, Pasadena, Calif., assignors to Monrovia Nursery Company, Monrovia, Calif., a corporation of California Application June 27, 1952, Serial No. 296,100

1 Claim. (Cl. 47—60)

Our present invention relates to a new and distinct variety of azalea plant of the Belgian Indica type and is the result of definite breeding efforts. The cross which produced the new variety was made between the varieties Paul Schame and Simon Mardner (both unpatented) at the home of the latter-named inventor in Pasadena, California. Asexual reproduction by the first-named inventor was accomplished in southern California by means of cuttings and has shown that the characteristics of the new variety are apparently permanent.

The principal distinction of our new variety of azalea lies in the color and form of its flower, it being much like its parents in many other respects, with the exception that it blooms mid-season—earlier than one parent and later than the other.

The accompanying illustrations show a black-and-white photograph of a young potted plant of our new variety, with a single flower and small branch below, shown in their natural colors as nearly true as the artist could make them.

In the following detailed description of our new variety, color plate references are to the Horticultural Chart by the British Colour Council, and other color names indicate the usual dictionary meaning of the word.

*The plant*

Form: The plant grows in a round, semi-compact form.

Growth habits: This variety is primarily a forcing variety but will grow outside if temperatures are not too low. It has a moderate rate of growth as compared with most Belgian Indicas. It roots well, making reproduction easy.

Cold resistance: This variety will endure tempertures as low as 24 degrees Fahrenheit.

Blooming season: In southern California the blooming season is from December through March. This variety blooms earlier than its parent Simon Mardner and later than its parent Paul Schame.

Blooming habits: The flowers of this variety occur in terminal, umbel-like racemes or clusters, with usually 3 to 5 blooms in a cluster. The quantity of bloom is comparable to that of its parents.

Stems: Woody, strong and sturdy.

Foliage:

*Density and persistence.*—Moderately dense and very persistent—blooming inhibiting its growth only temporarily.

*Color.*—Spinach Green 0960. Color of foliage remains approximately the same throughout the year.

*Size.*—Leaves range from 1 to 1½ inches in length and from ¼ to ½ inch in width.

*Shape.*—Obovate, with acute base and aristate apex. Entire.

*Surface appearance.*—Pubescent.

*Arrangement.*—Alternate on stem.

*The bloom*

Flowers:

*Borne.*—In umbel-like racemes of 3 to 5 flowers.

*Size.*—Large, measuring 3 to 3½ inches in diameter.

*Form.*—Open campanulate, with ten to fifteen petaloids, some approaching the size of the petals.

*Permanence.*—Individual flowers last from 1 to 2 weeks.

*Stem.*—Average length of flower stem is approximately ½ inch.

*Petalage.*—Five petals, with numerous petaloids of almost petal size, giving a double effect to the flower.

Petals:

*Shape.*—Approximately round and slightly ruffled; connected at base.

*Size.*—½ to ¾ inch in diameter.

*Texture.*—Good but not heavy.

*Color.*—Overall Phlox Pink, 625/2, with the marginal edge or rim of Phlox Pink 625. The effect of the coloring is picotee-like and this feature is one of the principal points of differentiation between the new variety and its parent Simon Mardner. After severance, the flower color increases in intensity after several hours, and also appears to have a slight magenta cast.

Reproductive organs:

*Stamens.*—Modified, becoming petaloids in most cases. One or two petaloids in each flower may retain stamen-like structures but most of them are petal-like. Color of the petaloids is the same as that of the petals but may appear to be of deeper intensity.

*Pistil.*—Persistent; approximately 1 inch in length; same color as the petaloids.

*Comparisons*

The variety Simon Mardner, one of its parents, is the variety most like our new variety, but differs principally as follows:

1. The color of the flower of our new variety is less intense than that of Simon Mardner.

2. The color of the flower of our new variety is picotee-like, whereas that of Simon Mardner is of approximately unvarying intensity throughout, even on the petal edges.

3. The form of the flowers of the two varieties is different, in that our new variety has a greater quantity of irregularly shaped petaloids, giving the flower a rather full, double appearance in contrast with the single appearance of Simon Mardner.

4. The blooming season of our new variety is earlier than that of Simon Mardner.

Our new variety also resembles its parent, Paul Schame, but differs principally in the following respects:

1. The color of the flowers differs in that the flower of Paul Schame is salmon pink and the flower of our new variety is light phlox pink with a petal rim of darker phlox pink.

2. The form of the flowers of the two varieties differs because the center of our new variety has more petaloids, some approaching the size of petals, thus making a much fuller flower.

3. The blooming season of our new variety is later than that of Paul Schame.

Having thus disclosed our invention, we claim:

The new and distinct variety of evergreen azalea plant of the Belgian Indica class, substantially as herein shown and described, characterized particularly by its mid-season blooming period; its ease of reproduction by rooting; and its picotee-like, phlox pink flowers of open campanulate form with many central petaloids producing a double bloom effect.

WILLIAM B. MULHOLLAND.
PAUL E. SHEPP.

No references cited.